United States Patent [19]

Yamasaki et al.

[11] Patent Number: 4,459,396

[45] Date of Patent: Jul. 10, 1984

[54] PROCESS FOR PRODUCING WATER-ABSORBENT MATERIALS HAVING EXCELLENT WATER ABSORPTION PROPERTIES

[75] Inventors: Harumasa Yamasaki; Yuzo Sumida; Shoichiro Harada, all of Wakayama, Japan

[73] Assignee: Kao Soap Co., Ltd., Tokyo, Japan

[21] Appl. No.: 402,692

[22] Filed: Jul. 28, 1982

[30] Foreign Application Priority Data

Aug. 20, 1981 [JP] Japan .................................. 55-130670

[51] Int. Cl.$^3$ .............................................. C08F 2/24
[52] U.S. Cl. .................................... 526/200; 526/288; 526/317; 526/306
[58] Field of Search ............... 526/200, 287, 288, 240, 526/303.1, 317, 306, 320

[56] References Cited

U.S. PATENT DOCUMENTS

| | | | |
|---|---|---|---|
| 2,982,749 | 5/1961 | Friedrich et al. | 526/240 |
| 3,929,741 | 12/1975 | Laskey | 526/288 |
| 3,951,528 | 4/1976 | Leeds | 526/200 |
| 4,286,082 | 8/1981 | Tsubakimoto et al. | 526/240 |
| 4,340,706 | 7/1982 | Obayashi | 526/240 |

FOREIGN PATENT DOCUMENTS

| | | | |
|---|---|---|---|
| 55-133413 | 10/1980 | Japan | 526/240 |
| 56-76419 | 6/1981 | Japan | 526/200 |

*Primary Examiner*—Joseph L. Schofer
*Assistant Examiner*—Peter F. Kulkosky
*Attorney, Agent, or Firm*—Flynn, Thiel, Boutell & Tanis

[57] ABSTRACT

A process is disclosed for producing a water-absorbent material by dispersing and suspending an aqueous solution of a water-soluble, ethylenically unsaturated monomer in a hydrocarbon or halogenated aromatic hydrocarbon in the presence of an oil-soluble cellulose ester or cellulose ether and then carrying out the polymerization using a water-soluble radical-polymerization initiator, characterized by the feature that one or more water-soluble or water-dispersible surfactants is (are) added to the system during or after the polymerization reaction.

16 Claims, No Drawings

PROCESS FOR PRODUCING WATER-ABSORBENT MATERIALS HAVING EXCELLENT WATER ABSORPTION PROPERTIES

The present invention relates to a process for producing a water-insoluble, water-absorbent material capable of absorbing a large quantity of an aqueous liquid and stably retaining it.

More particularly, the present invention relates to a process for producing a water-insoluble, water-absorbent material having a high initial water absorbency and a high capacity to absorb not only water, but also blood and aqueous solutions of one or more salts.

Papers, pulps and sponges have been used as water-absorbent materials or water-retaining materials in the production of sanitary products, such as sanitary napkins and paper diapers, and in the agricultural field. However, these materials have a low water-absorption capacity, and a great part of the water that is absorbed therein is squeezed out if pressure is applied thereto. As new water-absorbent materials usable in place of the conventional water-absorbent materials, there have been recently proposed several water-absorbent materials, such as starch/acrylonitrile graft copolymer hydrolyzates, modified cellulose ethers and methyl acrylate/vinyl acetate copolymer hydrolyzates. Further, these materials have been improved in various ways. However, their water absorption properties are still unsatisfactory because their respective capacities to absorb aqueous salt solutions are insufficient, even though they have an excellent water absorbency.

The present inventors previously proposed water-absorbent materials having improved water-absorption properties [Japanese patent application Nos. 43488/1981 (corresponding to U.S. patent application Ser. No. 360,496, filed Mar. 22, 1982) and 43489/1981], the entire contents of which are incorporated herein by reference. The specifications of these patent applications disclose a process for producing highly water-absorbent polymers which comprises dispersing and suspending an aqueous solution of water-soluble, ethylenically unsaturated monomer containing, if necessary, up to 5 wt. % of a cross-linking agent, in a hydrocarbon or halogenated aromatic hydrocarbon liquid phase, in the presence of an oil-soluble cellulose ester or cellulose ether that acts as a protective colloid, and then carrying out the polymerization reaction, in the presence of a water-soluble radical-polymerization initiator. However, these water-absorbent polymers have a defect in that they exhibit a relatively low rate of absorbing aqueous salt solutions or blood, although they exhibit a high rate of absorbing water. After intensive investigations made for the purpose of overcoming this defect, the inventors have discovered that a water-absorbent polymer, that exhibits a high rate of absorbing aqueous salt solutions or blood, can be obtained by adding one or more water-soluble and/or water-dispersible surfactants to the polymer slurry during or after the polymerization reaction, in the production of a highly water-absorbent polymer by the above-described polymerization method. The present invention has been completed on the basis of this finding.

The present invention provides a process for producing a water-insoluble, water-absorbent polymer material by dispersing and suspending an aqueous solution of a water-soluble, ethylenically unsaturated monomer in a liquid hydrocarbon or liquid halogenated aromatic hydrocarbon, in the presence of an oil-soluble cellulose ester or cellulose ether that acts as a protective colloid, and then carrying out the polymerization using a water-soluble radical-polymerization initiator, characterized by the improvement that one or more water-soluble and/or water-dispersible surfactants is(are) added to the system during the polymerization reaction or after the polymerization reaction is completed.

As the water-soluble or water-dispersible surfactants that are used in the present invention, there can be mentioned (1) nonionic surfactants having a hydrophile-lipophile balance (HLB) of 7 or higher, such as polyoxyethylene alkyl ethers, polyoxyethylene alkylphenol ethers, polyoxyethylene sorbitan fatty acid esters, polyoxyethylene fatty acid esters and poly(oxyethylene/oxypropylene) block copolymers, (2) anionic surfactants, such as fatty acid salts, alkylnaphthalenesulfonates, dialkyl sulfosuccinates, alkylsulfuric acid ester salts and higher alcohol sulfate ester salts, and (3) cationic surfactants, such as alkylamine salts and alkyl quaternary ammonium salts. Among these surfactants, nonionic surfactants and anionic surfactants, both having an HLB of 7 or higher, are particularly preferred. A combination of two or more of the above surfactants can be used. However, a combination of an anionic surfactant with a cationic surfactant is preferably avoided because they are likely to be incompatible with each other.

The water-soluble or water-dispersible surfactant(s) is(are) used in a total amount of 0.01 to 10 wt. %, preferably 0.05 to 5 wt. % and particularly 0.1 to 5 wt. %, based on the weight of (1) the polymer present in the polymerization reaction mixture when the surfactant is added after the polymerization is completed, or (2) the monomer charged into the polymerization system when the surfactant is added during polymerization. If the amount of the surfactant is less than 0.01 wt. %, the resulting water-absorbent polymer will exhibit a low salt solution-absorption rate. If the amount of the surfactant exceeds 10 wt. %, the resulting water-absorbent polymer has seriously deteriorated powder properties.

As the water-soluble, ethylenically unsaturated monomers used in the present invention, there can be mentioned, for example, (meth)acrylic acid, (meth)acrylic acid salts such as sodium and ammonium salts, (meth)acrylamide and N-substituted (meth)acrylamides, 2-(meth)acryloylethanesulfonic acid, 2-(meth)acryloylethanesulfonic acid salts, styrenesulfonic acid, styrenesulfonic acid salts and 2-hydroxyethyl (meth)acrylate. The term "(meth)acrylic" and the like means "acrylic" and "methacrylic."

Preferred monomers include sodium acrylate, acrylamide, 2-acrylamido-2-methylpropanesulfonic acid and sodium styrenesulfonate. These monomers can be used either singly or in the form of a mixture of two or more of them.

If necessary, the monomers can be polymerized in the presence of a water-soluble cross-linking agent having two or more reactive groups.

As the water-soluble cross-linking agents, there can be mentioned, for example N,N'-methylenebis (meth)acrylamide, N-methylol(meth)acrylamide, glycidyl (meth)acrylate, polyethylene glycol di(meth)acrylate, polyvalent metal salts of (meth)acrylic acid, phospho(meth)acrylate and polyol polyglycidyl ethers, such as ethylene glycol diglycidyl ether, glycerol tridiglycidyl ether and polyethylene glycol diglycidyl ether.

The amount of the cross-linking agent is generally variable over a wide range. However, the use of a large amount of the cross-linking agent is not preferred in the present invention, because it causes a reduction or disappearance of the swelling properties. For obtaining a highly-swellable, water-absorbent polymer, it is preferred to use the cross-linking agent in an amount of up to 5 wt. %, based on the weight of the water-soluble ethylenically unsaturated monomer.

The monomer concentration of the aqueous monomer solution is generally variable over a broad range. From an economic viewpoint, however, desirable concentrations range from 30 wt. % to the saturation concentration, preferably from 35 wt. % to the saturation concentration.

The cellulose ester or cellulose ether is oil-soluble at the polymerization temperature. It is used as a protective colloid in the W/O emulsion polymerization according to the present invention. It is insoluble or sparingly soluble in the liquid hydrocarbon or liquid halogenated aromatic hydrocarbon used as a dispersion medium at room temperature, but it is soluble therein at the polymerization temperature (about 40° C.).

As the cellulose ester or ether, there can be mentioned, for example, cellulose acetate, cellulose propionate, cellulose butyrate, cellulose acetate propionate, cellulose acetate butyrate, cellulose acetate phthalate, ethylcellulose, benzylcellulose or ethylhydroxyethylcellulose. In particular, cellulose acetate butyrate, ethylcellulose or ethylhydroxyethylcellulose is preferred. The protective colloid is used in an amount of 0.1 to 15 wt. %, preferably 0.5 to 10 wt. %, based on the weight of the monomer.

As the oil phase of the W/O emulsion, used in the present invention, liquid hydrocarbons or liquid halogenated aromatic hydrocarbons having 6 to 10 carbon atoms are preferred. Such materials include, for example, aromatic hydrocarbons, such as benzene and toluene, alicyclic hydrocarbons, such as cyclohexane, cyclooctane and decalin, aliphatic hydrocarbons, such as hexane and heptane, and halogenated aromatic hydrocarbons, such as chlorobenzene, bromobenzene and dichlorobenzene. The preferred solvents are toluene, xylene, cyclohexane, methylcyclohexane, hexane, heptane, chlorobenzene and dichlorobenzene. These solvents can be used as the dispersion medium either singly or in the form of a mixture of two or more of them, depending on the type of cellulose ester or ether employed. It is industrially advantageous to use only one solvent, because a single solvent can be recycled easily. If one of toluene, xylene, ethylbenzene, chlorobenzene or dichlorobenzene is used as the sole dispersion medium, suitable cellulose derivatives for use therewith are ethylcellulose having an ethoxy group content of 43 to 47 wt. % or cellulose acetate butyrate having a butyryl group content of 20 to 50 wt. %. If one of cyclohexane, cyclopentane, methylcyclohexane or decalin is used as the sole dispersion medium, a suitable cellulose derivative is ethylcellulose having an ethoxy group content of 47 to 50 wt. %. If one of n-hexane, n-heptane or n-octane is used as the sole dispersion medium, a suitable cellulose derivative is ethylhydroxyethylcellulose.

The proportion (volume ratio) of the dispersion medium to the aqueous monomer solution, the latter forming the dispersed phase of the W/O emulsion, is variable over a broad range. However, in view of the need for removal of the heat of the polymerization and control of the polymerization temperature, a ratio of (dispersion medium):(aqueous monomer solution) in the range of 1:2 to 5:1 is generally preferred.

For carrying out the polymerization of the monomer, a water-soluble radical-polymerization initiator, such as a persulfate, for example, potassium persulfate or ammonium persulfate, a hydroperoxide, for example, t-butyl hydroperoxide or cumene hydroperoxide, or an azo compound, for example 2,2'-azobis-2-amidinopropane hydrochloride, is used in a conventional amount. These initiators can be used also in the form of a mixture of two or more thereof. Further, they can be used as redox initiators.

Among the initiators mentioned above, the persulfates are preferred. In particular, when the self-cross-linking reaction must be carried out in the absence of any cross-linking agent, the persulfate should be used.

According to the present invention, the water-soluble and/or water-dispersible surfactants can be added to the reaction system during the polymerization or to the polymer slurry after completion of the polymerization. The addition method is selected according to the type of surfactant employed. Generally, however, it is preferred to add the surfactant to the polymer slurry after completion of the polymerization.

The mechanism of the high absorbency rate exhibited by the water-absorbent polymer obtained by the process of the present invention has not fully been elucidated, but it is considered that the surfactant breaks the protective colloid film covering the water-absorbent polymer particles and cause the entire water-absorbent polymer to be penetrable by water, aqueous salt solutions and blood. However, the details of this mechanism are still unclear.

According to the process of the present invention, it becomes possible to obtain a water-absorbent polymer material that exhibits a high rate of absorption of a salt solution or blood. The absorbent materials obtained by the process of the present invention can be used as agricultural water-retaining agents or dehydrating agents for removing water directly from a mixture of an oil and water, or as materials for hygienic products. The absorbent materials of the invention can be used for the production of paper diapers capable of absorbing a large quantity of urine or as an absorbent material in sanitary napkins capable of absorbing menses blood without problems of leakage or unpleasant feeling.

The following illustrative examples and comparative examples further describe the present invention but they do not limit the scope of the invention.

The absorbent capacity in the following examples and comparative examples was determined as follows: about 1 g of polymer was dispersed in a large excess of physiological saline solution and was swollen sufficiently until no further absorption occurred. The dispersion was filtered through a 80 mesh metal gauze and the resulting swollen polymer was weighed. The obtained value (W) was divided by the initial weight of the polymer (Wo) to obtain the value of Absorbent Capacity, as follows:

Absorbent Capacity (g/g)=W/Wo.

The absorption rate was determined by measuring the quantity of physiological saline or artificial blood that was absorbed by 0.5 g of polymer in 10 minutes. The artificial blood comprised 30 wt. % of glycerol, 0.9 wt. % of common salt (NaCl), 0.0025 wt. % of Emulgen 935 (polyoxyethylene (35 mol) nonylphenol ether, a product of Kao Atlas Co., Ltd.), 0.01 wt. % of Red Dye No. 2 and the balance was deionized water.

EXAMPLE 1

1150 ml of cyclohexane and 3.64 g of ethyl cellulose (Ethylcellulose N-22, a product of Hercules Inc., ethoxy group content: 47.5–49 wt. %) were charged in a 2 l four-necked, round-bottom flask provided with a stirrer, reflux condenser, dropping funnel and nitrogen gas-inlet tube. Nitrogen gas was introduced therein to purge dissolved oxygen. The temperature was elevated to 75° C. In a separate flask, 150 g of acrylic acid was neutralized with 65.8 g of 98% sodium hydroxide dissolved in 200 g of deionized water, under external cooling. The monomer concentration in the thus-formed aqueous solution was 45 wt. %. Then, 0.5 g of potassium persulfate and 0.15 g of N,N'-methylenebisacrylamide were dissolved in the aqueous solution and nitrogen was introduced into the solution to remove oxygen present therein. The contents of the latter flask were added dropwise to the contents of the first-mentioned four-necked flask over a period of one hour. After completion of the addition, the mixture was kept at 75° C., the reaction was continued for 2 hours and then the reaction mixture was then cooled to 40° to 50° C. 1.82 g of polyoxyethylene lauryl ether [EO (ethylene oxide) addition mol number=average of 35] was dissolved therein. The cyclohexane was distilled out under reduced pressure and the remaining swollen polymer was dried at 80° C. to 150° C. under reduced pressure to obtain 190.1 g of the intended polymer product (particle size: 100–350μ).

EXAMPLE 2

The same procedure as described in Example 1 was repeated, except that 0.75 g of polyethylene glycol diglycidyl ether (n=9) was used as a cross-linking agent and 1.82 g of Pelex OT-P (sodium dialkyl sulfosuccinate, a product of Kao Atlas Co., Ltd.) was used as a surfactant. There were obtained 190.2 g of polymer particles (particle size: 100–350μ).

EXAMPLE 3

The same procedure as described in Example 1 was repeated, except that 0.18 g of polyoxyethylene (30 ml) nonylphenyl ether was added as a surfactant after completion of the polymerization. There were obtained 188.1 g of polymer particles (particle size: 100–350μ).

EXAMPLE 4

1150 ml of hexane and 13.02 g of ethylhydroxyethylcellulose (E.H.E.C. Low, a product of Hercules Inc.) were charged into the same polymerization reactor as employed in Example 1 and heated to 65° C. In a separate flask, 130 g of acrylic acid and 20 g of 2-acrylamido-2-methylpropanesulfonic acid were neutralized with 61.0 g of 98% sodium hydroxide dissolved in 220 g of deionized water. 0.5 g of ammonium persulfate and 3 g of the crosslinking agent polyethylene glycol dimethacrylate (n=14) were dissolved therein to obtain an aqueous monomer solution. The polymerization was carried out in the same manner as described in Example 1. Then, 0.36 g of polyoxyethylene (20 mol) stearyl ether was dissolved into the polymer suspension at 40° to 50° C. There were obtained 196.2 g of a polymer (particle size: 100–350μ) in the same manner as described in Example 1.

EXAMPLE 5

An aqueous monomer solution (120 g of acrylic acid), the same as the one used in the polymerization recipe of Example 1, was neutralized with 51.0 g of 98% sodium hydroxide dissolved in 250 g of deionized water. Then, 30 g of acrylamide, 0.75 g of N-methylolacrylamide and 0.3 g of potassium persulfate were dissolved in the solution to obtain a monomer solution. After carrying out the polymerization in the same manner as described in Example 1, 2.1 g of Tween 40 (polyoxyethylene sorbitan monopalmitate, a product of Kao Atlas Co., Ltd.) was added to the polymerization reaction mixture. There were obtained 183.4 g of a polymer (particle size: 100–350μ) in the same manner as described in Example 1.

EXAMPLE 6

The polymerization reaction was carried out in the same manner as described in Example 1, except that 0.54 g of sodium oleate, used as a surfactant, was dispersed in the cyclohexane before the polymerization. There were obtained 190.1 g of the intended polymer (particle size: 100–350μ).

EXAMPLE 7

There was used the same aqueous monomer solution as the one used in Example 1, except that N,N'-methylene-bisacrylamide (cross-linking agent) was excluded. The aqueous monomer solution was added in two portions to the polymerization system. The mixture was kept at 70° C. to 75° C. for 1 hour after completion of the polymerization, and then it was cooled to 40° C. to 50° C. 1.6 g of polyoxyethylene (25 mol) stearyl ether was dissolved therein. Then, the same procedure as described in Example 1 was repeated. There were obtained 191.4 g of the intended polymer (particle size: 100–250μ).

Comparative Examples 1 to 7

The same procedures as described in Examples 1 to 7 were repeated, except that the surfactants were omitted. The yields and particle sizes were equal to those in Examples 1 to 7.

The absorbent capacity and absorption rates of the polymers obtained in Examples 1 to 7 and Comparative Examples 1 to 7 are shown in Table 1.

TABLE 1

| Experiment No. | Absorbent Capacity (Physiological Saline) (g/g) | Absorption Rate (0.5 g of polymer, for 10 min.) | |
|---|---|---|---|
| | | Physiological Saline (ml) | Artificial Blood (ml) |
| Example 1 | 58 | 18 | 7.5 |
| Example 2 | 60 | 21 | 6.0 |
| Example 3 | 59 | 18.5 | 7.0 |
| Example 4 | 55 | 17.8 | 5.8 |
| Example 5 | 53 | 18.0 | 6.5 |
| Example 6 | 58 | 17.0 | 6.2 |
| Example 7 | 68 | 13 | 5.0 |
| Comparative Example 1 | 58 | 10.8 | 3.0 |
| Comparative Example 2 | 60 | 9.9 | 3.0 |
| Comparative Example 3 | 59 | 10.2 | 2.8 |
| Comparative Example 4 | 55 | 9.4 | 2.0 |
| Comparative Example 5 | 53 | 9.8 | 2.5 |

TABLE 1-continued

| Experiment No. | Absorbent Capacity (Physiological Saline) (g/g) | Absorption Rate (0.5 g of polymer, for 10 min.) | |
|---|---|---|---|
| | | Physiological Saline (ml) | Artificial Blood (ml) |
| Comparative Example 6 | 58 | 10.0 | 2.8 |
| Comparative Example 7 | 68 | 7.0 | 1.8 |

It is apparent from Table 1 that the polymers obtained according to the present invention have excellent capacities for absorbing salt solutions and blood, and particularly for more rapid absorption of salt solutions or artificial blood, compared to the comparative examples lacking the surfactant.

The entire contents of the U.S. patent application Ser. No. 360,496, filed Mar. 22, 1982, entitled "PROCESS FOR PREPARATION OF HIGH WATER-ABSORBENT POLYMER BREADS," by Applicants Yamasaki and Harada, corresponding to Japanese patent application No. 43488/81 filed Mar. 25, 1981, are hereby incorporated by reference in this specification.

The embodiments of the invention in which an exclusive property or privilege is claimed are defined as follows:

1. A process for preparing a water-insoluble polymer capable of absorbing water, aqueous salt solutions and blood, which comprises the steps of:
    dispersing (1) an aqueous solution of a water-soluble ethylenically unsaturated monomer, said solution containing from 30% by weight up to the saturation amount of said monomer, in (2) a liquid dispersion medium selected from the group consisting of hydrocarbon liquids and halogenated aromatic hydrocarbon liquids, so that the volume ratio of said dispersion medium to said aqueous solution is in the range of 1:2 to 5:1, in the presence of from 0.1 to 15% by weight, based on the weight of said monomer, of a protective colloid selected from the group consisting of cellulose esters and cellulose ethers, thereby forming a water-in-oil dispersion, said protective colloid being insoluble or sparingly soluble in said dispersion medium at room temperature;
    then polymerizing said monomer, at an elevated temperature of at least 40° C., in the presence of a water-soluble radical polymerization initiator, whereby to form particles of a polymer dispersed in said liquid dispersion medium, said protective colloid being soluble in said dispersion medium at said elevated polymerization temperature;
    adding from 0.01 to 10% by weight, based on the weight of said monomer, of one or more water-soluble or water-dispersible surfactants having an HLB of 7 or higher to the liquid dispersion medium during or after completion of said polymerization step; and
    then recovering said polymer particles.

2. A process as claimed in claim 1, wherein said surfactant is selected from the group consisting of nonionic surfactants having an HLB of 7 or higher, anionic surfactants having an HLB of 7 or higher, and mixtures thereof.

3. A porcess as claimed in claim 1, wherein said aqueous solution contains a water-soluble cross-linking agent in an amount not greater than 5 wt. %, based on the weight of said monomer, and effective to cause cross-linking of said polymer.

4. A process according to claim 1, wherein said surfactant is selected from the group consisting of polyoxyethylene alkyl ethers, polyoxyethylene alkylphenol ethers, polyoxyethylene sorbitan fatty acid esters, polyoxyethylene fatty acid esters, poly(oxyethylene/oxypropylene) block copolymers, fatty acid salts, alkylnaphthalenesulfonates, dialkyl sulfosuccinates, alkylsulfuric acid ester salts, higher alcohol sulfate ester salts, alkylamine salts, alkyl quaternary ammonium salts and compatible mixtures thereof.

5. A process according to claim 1, wherein said ethylenically unsaturated monomer is selected from the group consisting of acrylic acid, methacrylic acid, acrylic acid salts, methacrylic acid salts, acrylamide, methacrylamide, N-substituted acrylamides, N-substituted methacrylamides, 2-acryloylethanesulfonic acid, 2-methacryloylethanesulfonic acid, 2-acryloylethanesulfonic acid salts, 2-methacryloylethanesulfonic acid salts, styrenesulfonic acid, styrenesulfonic acid salts, 2-hydroxyethyl acrylate and 2-hydroxyethyl methacrylate.

6. A process according to claim 1, wherein said ethylenically unsaturated monomer is selected from the group consisting of sodium acrylate, acrylamide, 2-acrylamido-2-methylpropanesulfonic acid, sodium styrenesulfonate and mixtures thereof.

7. A process according to claim 1, wherein said protective colloid is selected from the group consisting of cellulose acetate butyrate, ethylcellulose and ethylhydroxyethylcellulose.

8. A process according to claim 1, wherein said hydrocarbon and halogenated aromatic hydrocarbon have from 6 to 10 carbon atoms.

9. A process according to claim 1, wherein said dispersion medium is selected from the group consisting of toluene, xylene, cyclohexane, methylcyclohexane, hexane, heptane, chlorobenzene, dichlorobenzene and mixtures thereof.

10. A process as claimed in claim 1, wherein said dispersion medium is selected from the group consisting of toluene, xylene, ethylbenzene, chlorobenzene and dichlorobenzene, and said protective colloid is selected from the group consisting of ethylcellulose having an ethoxy group content of 43 to 47 wt. % and cellulose acetate butyrate having a butyryl group content of 20 to 50 wt. %.

11. A process according to claim 1, wherein said dispersion medium is selected from the group consisting of cyclohexane, cyclopentane, methylcyclohexane and decalin, and said protective colloid is ethylcellulose having an ethoxy group content of 47 to 50 wt. %.

12. A process according to claim 1, wherein said dispersion medium is selected from the group consisting of n-hexane, n-heptane and n-octane, and said protective colloid is ethylhydroxyethylcellulose.

13. A water-absorbent polymeric material prepared by the process as claimed in claim 1.

14. A process as claimed in claim 1, wherein said surfactant is added after completion of said polymerization step.

15. A process for preparing a water-insoluble polymer capable of absorbing water, aqueous salt solutions and blood, which comprises the steps of:
    dispersing an aqueous solution consisting essentially of at least 30 percent by weight of a water-soluble, ethylenically unsaturated monomer, in a liquid dispersion medium consisting of a hydrocarbon liquid or halogenated aromatic hydrocarbon liquid, in the presence of 0.1 to 15 wt. %, based on the weight of said monomer, of a protective colloid selected from the group consisting of cellulose esters and cellulose ethers, said protective colloid being insoluble or sparingly soluble in said dispersion medium at room temperature, the volume ratio of said dispersion medium to said aqueous monomer solution being in the range of 1:2 to 5:1;

then polymerizing said monomer, in the presence of a water-soluble radical polymerization initiator, at an elevated polymerization temperature of at least 40° C., said protective colloid being soluble in said dispersion medium at said elevated polymerization temperature, whereby to form particles of a polymer dispersed in said liquid dispersion medium;

adding 0.01 to 10 wt. %, based on the weight of said monomer, of one or more water-soluble or water-dispersible surfactants selected from the group consisting of nonionic surfactants having an HLB of 7 or higher, anionic surfactants having an HLB of 7 or higher, and mixtures thereof, to the liquid dispersion medium during or after completion of said polymerization step; and then recovering said polymer particles.

16. A water absorbent polymeric material prepared by the process as claimed in claim 15.

* * * * *